US010995299B2

(12) United States Patent
Hermel-Davidock et al.

(10) Patent No.: US 10,995,299 B2
(45) Date of Patent: *May 4, 2021

(54) SELF-LUBRICATING POLYMER COMPOSITION

(71) Applicant: Becton, Dickinson and Company, Franklin Lakes, NJ (US)

(72) Inventors: Theresa Hermel-Davidock, Newton, NJ (US); Lisa Lim, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/959,377

(22) Filed: Apr. 23, 2018

(65) Prior Publication Data

US 2018/0237721 A1  Aug. 23, 2018

Related U.S. Application Data

(63) Continuation of application No. 14/805,620, filed on Jul. 22, 2015.

(60) Provisional application No. 62/027,840, filed on Jul. 23, 2014.

(51) Int. Cl.
| | | |
|---|---|---|
| *C10M 155/02* | (2006.01) | |
| *A61L 29/06* | (2006.01) | |
| *A61L 31/06* | (2006.01) | |
| *A61L 31/14* | (2006.01) | |
| *C08G 18/48* | (2006.01) | |
| *C08G 18/61* | (2006.01) | |
| *C08G 18/66* | (2006.01) | |
| *C08G 18/76* | (2006.01) | |
| *C08G 18/32* | (2006.01) | |

(52) U.S. Cl.
CPC .......... *C10M 155/02* (2013.01); *A61L 29/06* (2013.01); *A61L 31/06* (2013.01); *A61L 31/14* (2013.01); *C08G 18/3206* (2013.01); *C08G 18/4854* (2013.01); *C08G 18/61* (2013.01); *C08G 18/6674* (2013.01); *C08G 18/7657* (2013.01); *A61L 2400/10* (2013.01)

(58) Field of Classification Search
CPC ............ C10M 155/02; C08G 18/3206; C08G 18/7657; C08G 18/6674; C08G 18/61; C08G 18/4854; A61L 31/14; A61L 31/06; A61L 29/06; A61L 2400/10
See application file for complete search history.

(56) References Cited

U.S. PATENT DOCUMENTS

| | | |
|---|---|---|
| 3,755,218 A * | 8/1973 | Yen ..................... A61L 33/0023 428/35.5 |
| 4,058,506 A | 11/1977 | Vaeth et al. |
| 4,647,643 A | 3/1987 | Zdrahala et al. |
| 5,026,814 A | 6/1991 | Re et al. |
| 5,032,666 A | 7/1991 | Hu et al. |
| 5,043,410 A | 8/1991 | Re et al. |
| 5,226,899 A | 7/1993 | Lee et al. |
| 5,262,057 A | 11/1993 | Tonelli et al. |
| 5,332,798 A | 7/1994 | Ferreri et al. |
| 5,453,099 A | 9/1995 | Lee et al. |
| 5,508,380 A | 4/1996 | Turri et al. |
| 5,589,563 A | 12/1996 | Ward et al. |
| 6,207,777 B1 | 3/2001 | Shimada et al. |
| 6,268,440 B1 | 7/2001 | Kudo et al. |
| 6,287,707 B1 | 9/2001 | Luthra et al. |
| 6,313,254 B1 | 11/2001 | Meijs et al. |
| 6,579,835 B2 | 6/2003 | Scicchitano et al. |
| 7,358,306 B2 | 4/2008 | Turri et al. |
| 8,357,767 B2 | 1/2013 | Moore et al. |
| 9,334,213 B2 | 5/2016 | Guarda et al. |
| 9,345,806 B2 | 5/2016 | Tonelli et al. |
| 2003/0018156 A1* | 1/2003 | Meijs ..................... A61L 15/26 528/26 |
| 2003/0114605 A1 | 6/2003 | Harris et al. |
| 2005/0025966 A1 | 2/2005 | Vedula et al. |
| 2005/0261427 A1 | 11/2005 | Saito |
| 2013/0178125 A1 | 7/2013 | Jiang et al. |
| 2013/0183262 A1* | 7/2013 | Wynne ............... C08G 18/6674 424/78.3 |
| 2016/0024419 A1 | 1/2016 | Hermel-Davidock et al. |
| 2017/0107320 A1 | 4/2017 | Zhou et al. |
| 2017/0226272 A1 | 8/2017 | Cozzens et al. |
| 2017/0334034 A1 | 11/2017 | Kadowaki et al. |
| 2018/0105665 A1 | 4/2018 | Day et al. |
| 2019/0111186 A1 | 4/2019 | Lyu et al. |
| 2019/0112411 A1 | 4/2019 | Chen et al. |

(Continued)

FOREIGN PATENT DOCUMENTS

| | | |
|---|---|---|
| AU | 2010224421 B9 | 12/2010 |
| AU | 2015206417 B2 | 7/2015 |
| CA | 2716502 C | 11/2010 |

(Continued)

OTHER PUBLICATIONS

PCT International Search Report and Written Opinion in PCT/US2018/026250, dated Jul. 6, 2018, 16 pgs.
PCT Preliminary Report on Patentability for PCT/US2016/056738, dated Apr. 26, 2018, 9 pgs.
PCT International Preliminary Report on Patentability in PCT/US2015/041679 dated Feb. 2, 2017, 9 pages.
PCT International Search Report and Written Opinion in PCT/US2015/041679, dated Oct. 12, 2015, 112 pages.

(Continued)

*Primary Examiner* — Taiwo Oladapo

(74) *Attorney, Agent, or Firm* — Servilla Whitney LLC

(57) ABSTRACT

A polymer resin composition is disclosed including a chemically attached lubricant structure to produce a self-lubricating medical device thereby eliminating the need of a secondary lubrication step currently required which is useful in medical and surgical devices.

12 Claims, No Drawings

(56) References Cited

U.S. PATENT DOCUMENTS

2019/0388593 A1  12/2019  Miura et al.

FOREIGN PATENT DOCUMENTS

| | | |
|---|---|---|
| CA | 2937132 A1 | 7/2015 |
| CN | 102316965 A | 1/2012 |
| DE | 19619327 A1 | 11/1997 |
| DE | 10050495 A1 | 4/2002 |
| DE | 102016225500 A1 | 6/2018 |
| EP | 0359273 A2 | 3/1990 |
| EP | 0448886 A1 | 10/1991 |
| EP | 0472413 A2 | 2/1992 |
| EP | 0824932 A2 | 2/1998 |
| EP | 0914836 A2 | 5/1999 |
| EP | 0962227 A1 | 12/1999 |
| EP | 2517828 A1 | 10/2012 |
| GB | 2332438 A | 6/1999 |
| JP | 58165836 A | 9/1983 |
| JP | 60252617 A | 12/1985 |
| WO | 95/26993 A1 | 10/1995 |
| WO | 2002/010244 A2 | 2/2002 |
| WO | 2006042739 A1 | 4/2006 |
| WO | 2011065432 A1 | 6/2011 |
| WO | 2012027729 A1 | 3/2012 |
| WO | 2016172460 A1 | 10/2016 |
| WO | 2017014597 A1 | 1/2017 |
| WO | 2017015072 A1 | 1/2017 |
| WO | 2017015073 A1 | 1/2017 |
| WO | 2017172740 A1 | 10/2017 |
| WO | 2018011748 A1 | 1/2018 |
| WO | 2018029133 A1 | 2/2018 |
| WO | 2018140911 A1 | 8/2018 |
| WO | 2018194840 A1 | 10/2018 |
| WO | 2019101771 A1 | 5/2019 |
| WO | 2020021203 A1 | 1/2020 |
| WO | 2020030670 A1 | 2/2020 |
| WO | 2020068617 A1 | 4/2020 |
| WO | 2020068619 A1 | 4/2020 |

OTHER PUBLICATIONS

Wang, et al., "Friction and wear behavior of the polyurethane composites modifies by bishydroxyl-terminated polydimethylsiloxane", Industrial Lubrication and Tribology, vol. 65, No. 6, 2013, 472-479.
Solvay Specialty Polymers, "FLUOROLINK® for Low Surface Energy Coatings," 2013.
Arkles, Barry, et al., "Positive Tactile Interaction Coatings", Paint & Coatings Industry magazine, Issued Jul. 2017, vol. 23, No. 7, pp. 1-8.
Tonelli, Claudio, et al., "New Perfluoropolyether Soft Segment Containing Polyurethanes", Journal of Applied Polymer Science. vol. 57, 1031-1042 (1995).

* cited by examiner

SELF-LUBRICATING POLYMER COMPOSITION

CROSS-REFERENCE TO RELATED APPLICATIONS

This application is a continuation of and claims the benefit of priority of pending U.S. application Ser. No. 14/805,620, filed on Jul. 22, 2015, which claims priority under 35 U.S.C. § 119(e) to U.S. Provisional Application No. 62/027,840, filed Jul. 23, 2014, the disclosures of which are incorporated herein by reference in their entireties.

TECHNICAL FIELD

The present invention relates to a polymer resin composition including a chemically attached lubricant structure which may be used to produce a self-lubricating medical device thereby eliminating the need of a secondary lubrication step currently required.

BACKGROUND

Infusion therapy products have multiple components that require lubrication, including a cannula, catheter, wedge, tipping and blood control actuator. The lubricants are currently applied in a secondary, solvent-based process during the manufacture of the components. The solvents used during the secondary lubrication application process are constantly under scrutiny from regulatory agencies. Manufacturers are constantly seeking to upgrade their manufacturing processes to utilize acceptable solvents to ensure compliance with constantly changing regulatory standards. However, constant conversions and upgrades to manufacturing processes to comply with constantly changing regulatory standards, e.g. a conversion from the use of a HCFC solvents to a VOC-flammable solvent, can be both capital and resource intensive for the manufacturer. Thus, the elimination of the secondary, solvent based lubrication step would lead to substantial savings, not only from the elimination of the solvent but also with respect to the cost of the secondary process itself with regards to capital equipment, time and resources. The elimination of the secondary, solvent based lubrication step would also lead to a substantial environmental benefit and an increase in work-place safety resulting from the elimination of the solvent in the manufacturing process.

Lubricants which are applied as a coating or blended into the plastic itself can leach out into patient's blood stream. While the regulatory bodies currently allow for some controlled amount of silicone based (or other) lubricant into the patient. Thus, the elimination of the potential leaching would result in an increase to patient safety.

Thus, there is a need for a self-lubricating polymer composition which does not require a secondary, solvent based lubrication step while allowing for tailorability without additives or an extra coating. There is also a need for a self-lubricating polymer composition would also result in a consistent coating thickness and amount due to the lubricant being chemically-bounded to the resin, thereby mitigating concerns of variations of lubrication performance due to process variations. There is also a need for a functionalized lubricant which would eliminate migration concerns of the lubricant into the blood stream.

SUMMARY

One aspect is directed to a self-lubricating polyurethane composition comprising a reaction product of a diisocyanate and a diol mixture containing a short chain diol, a long chain polyether or polyester diol, and a lubricant. In one or more embodiments, the polyurethane has a lubricant chemically attached within the polyurethane resin. In one embodiment, the lubricant is incorporated into a backbone of the polyurethane resin. In one or more embodiments, the diisocyanate is selected from the group consisting of an aliphatic diisocyanate, alicyclic diisocyanate and an aromatic diisocyanate. In a more specific embodiment, the diisocyanate is selected from the group consisting of 4,4-diphenyl methane diisocyanate (MDI), toluene diisocyanate (TDI), isophorone diisocyanate (IPDI), and methylene bis (4-cyclohexyl isocyanate) (HMDI). In one or more embodiments, the short chain diol is selected from the group consisting of ethylene glycol, 1,3-propylene glycol, 1,4-butane diol, neopentyl glycol, and alicyclic glycols having up to 10 carbon atoms. In one or more embodiments, the polyether diol is a polyalkylene glycol. In one embodiment, the polyalkylene glycol is poly(tetramethylene ether) glycol. In one or more embodiments, the lubricant is a non-silicone diol, silicon diol, or fluorinated lubricant. In one embodiment, the silicon diol is polydimethylsiloxane diol. In a specific embodiment, the polydimethylsiloxane is present in an amount ranging from about 3 to 10 weight percent of the polyurethane composition. In one or more embodiments, the self-lubricating polyurethane composition includes an anti-microbial moiety covalently attached to the self-lubricating polyurethane. In one or more embodiments, the self-lubricating polyurethane composition includes an anti-thrombogenic moiety covalently attached to self-lubricating polyurethane. In one or more embodiments, the lubricant may be present in an amount ranging from about 1 to 10 weight percent of the polyurethane composition. In one or more embodiments, the lubricant is incorporated into a backbone formed by the diisocyanate and the diol mixture.

In one or more embodiments, the reaction further includes a catalyst selected from a group consisting of dibutyltin dilaurate, tertiary amines, and metallic compounds. In a specific embodiment, the tertiary amine is 1,4-diazabicyclo [2.2.2]octane). In a specific embodiment, the metallic compound is dibutyltin dilaurate or bismuth octanoate.

Another aspect is directed to a polyurethane of Formula I:

(I)

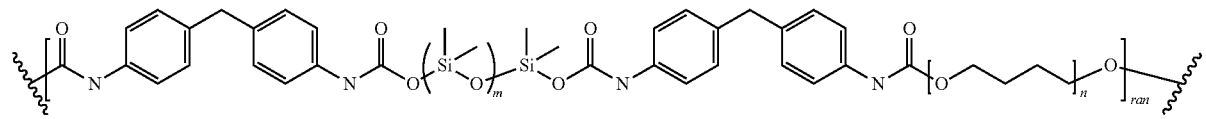

wherein the repeating unit of m is in the range from 5 to 2000; the repeating unit of n is in the range from 1 to 40 and the overall molecular weight of the polyurethane resins is between 15,000 g/mol to 130,000 g/mol.

Another aspect is directed to an article molded from the self-lubricated polyurethane composition disclosed herein. In one or more embodiments, the article is a component of a cannula, catheter, wedge, tipping, blood control actuator, or syringe. In a specific embodiment, the article is a stopper.

DETAILED DESCRIPTION OF THE INVENTION

Before describing several exemplary embodiments of the invention, it is to be understood that the invention is not limited to the details of construction or process steps set forth in the following description. The invention is capable of other embodiments and of being practiced or being carried out in various ways.

The present invention relates to a polyurethane resin having an incorporated lubricant structure which may be used to produce a self-lubricating medical device or component of a medical device. The resin of the present invention eliminates the required secondary lubrication step currently found in the manufacture of many medical device components. Due to the lower surface energy of an incorporated lubricant, the incorporated lubricant has a propensity for migration to the surface both during the catheter fabrication process and as a function of time post-production.

In one or more embodiments of the present invention, a lubricant is attached chemically to a polyurethane resin. In one or more embodiments, existing lubricants, such as polydimethylsiloxane or fluorinated lubricants, may be used. The lubricants are chemically reacted to attach with or be incorporated into a desired polyurethane resin of interest. In one or more embodiments, the lubricant is covalently attached or incorporated into the backbone structure of the resin. The lubricant may be attached chemically to a desired polyurethane resin using several techniques. One technique to chemically attach the lubricant to the desired polyurethane is the modification of the urethane monomer prior to polymerization of the monomer into a polyurethane polymer. In one embodiment, isocyante monomers are reacted with polyols to create polyurethane. The isocyante monomers can be modified to contain a lubricating moiety and the reaction with polyols will continue to create self-lubricating polyurethane.

Another technique to chemically attach the lubricant to the desired polyurethane is to graft a lubricant onto the resin backbone of an existing resin using controlled chemistry such as ATRP, functional group reactions, or plasma modification of the resin surface followed by grafting of the lubricant onto the surface of the resin.

Another technique to chemically attach the lubricant to the desired polyurethane is to utilize the functional groups on the lubricating chemicals to co-polymerize it with the monomers into a co-polymer thereby adding the lubricating moiety directly into the backbone of the polymer. For example, a lubricant, such as PDMS, can be made with alcohol or "OH" functional groups, which is an essential reactive group to the polyurethane synthesis. The structure of PDMS with the —OH functional group will co-react with the isocyanate to incorporate PDMS chains into polyurethane creating the self-lubricating polymer.

It is intended that the chemical modification process to functionalize the lubricant onto the resin would still enable the resin to be suitable for use in Class II medical devices.

During and after the fabrication process of the medical device component, the lubricant blooms to the surface due to the lower surface energies of the silicone or fluorinated groups. Due to the chemical linkage of the lubricant to the polymer chain of the bulk material, an additional lubrication process step to obtain the lubrication performance required is eliminated.

In another aspect of the present invention, the synthesis technique may also be utilized to incorporate anti-microbial chemicals or anti-thrombogenic chemicals into a polymer resin composition of the present invention including a lubricant structure.

The resin of the present invention may be used in polymer based medical devices which require lubrication such as the injection syringe barrel and/or stopper. The resin of the present invention may also be used in syringes which are prefilled with saline or other solutions which further dissolve the lubricant off the surface of the syringe barrel and carry it into the patient's bloodstream.

Example 1—PDMS-Polyurethane (Self-Lubricating Urethane)

A series of polyurethane resins of Formula I as follows were prepared:

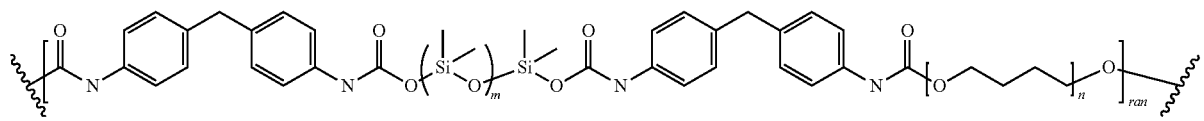

(I)

wherein the repeating unit of m is in the range from 5 to 2000. The repeating unit of n is in the range from 1 to 40. The overall molecular weight of the polyurethane resins is between 15,000 g/mol to 130,000 g/mol.

The polyurethane resins of Formula I were prepared from 400 g/mol to 77,000 g/mol of silicone fluid such as Gelest DMS-S31; polyols such as DuPont Tetrathane T-1000; 4,4-diphenyl methane diisocyanate (MDI); and 1,4 butanediol (BDO). The diols, i.e., DMS-S31, Tetrathane T-1000, and BDO were mixed, heated to 65±3° C. The MDI then was added and the mixture was stirred to prevent phase separation of the liquid mixture. After about 1 to 3 minutes, the temperature increased to about 80° C. The liquid mixture then was poured into polytetrafluoroethylene lined trays and heated to 100° C. overnight to complete the polymerization. After cooling to ambient temperature, the resins were chipped and extruded into film for measurement of physical properties. The results are showed in Table 1. As a control, sample #1 "0% PDMS", was prepared in which the DMS-S31 fluid was omitted and replaced with a like quantity of polyols. The results are also included in Table 1.

TABLE 1

Molecular Weight

|  | Number Avg. MW (Mn, g/mol) | Weight Avg. MW (Mw, g/mol) | Polydispersity (PDI = Mw/Mn) |
|---|---|---|---|
| 0% PDMS | 27,303 | 50,960 | 1.87 |
| 1% PDMS | 34,007 | 67,837 | 1.99 |
| 2% PDMS | 31,020 | 67,567 | 2.18 |
| 3% PDMS | 48,640 | 110,300 | 2.27 |
| 4% PDMS | 15,990 | 30,613 | 1.91 |
| 5% PDMS | 15,887 | 28,647 | 1.80 |
| 6% PDMS | 24,073 | 50,060 | 2.08 |
| 7% PDMS | 24,510 | 41,273 | 1.68 |
| 10% PDMS | 15,683 | 27,707 | 1.77 |

TABLE 2

Tensile Properties

|  | Avg. Tensile at break (Psi) | Std. dev. |
|---|---|---|
| 0% PDMS | 5887 | 1951 |
| 1% PDMS | 5684 | 965 |
| 2% PDMS | 6565 | 1645 |
| 3% PDMS | 6396 | 800 |
| 4% PDMS | 3574 | 457 |
| 5% PDMS | 2650 | 582 |
| 6% PDMS | N/A | N/A |
| 7% PDMS | 2157 | 582 |
| 10% PDMS | 1538 | 417 |

TABLE 3

Coefficient of Friction (CoF)

|  | Avg. Kinetic CoF |
|---|---|
| 0% PDMS | 0.295 |
| 0% PDMS dipped into 5% silicone catheter lube | 0.214 |
| 1% PDMS | 0.215 |
| 2% PDMS | 0.174 |
| 3% PDMS | 0.197 |
| 4% PDMS | 0.202 |
| 5% PDMS | 0.190 |
| 6% PDMS | 0.204 |
| 7% PDMS | 0.286 |
| 10% PDMS | 0.190 |

TABLE 4

Thermal Analysis

|  | Tc (° C.) | Tc Enthalpy (J/g) | Td (° C.) |
|---|---|---|---|
| 0% PDMS | 161.5 | 16.7 | 305 |
| 1% PDMS | ND | ND | 309 |
| 2% PDMS | ND | ND | 308 |
| 3% PDMS | ND | ND | 308 |
| 4% PDMS | ND | ND | 306 |
| 5% PDMS | ND | ND | 304 |
| 6% PDMS | ND | ND | 307 |
| 7% PDMS | ND | ND | 301 |
| 10% PDMS | ND | ND | 309 |

ND is defined as "not detected".

As shown in Tables 1-4, various Polyurethane/Polysiloxane resins were tested for various attributes such as number average molecular weight, weight average molecular weight, polydispersity, average tensile at break, coefficient of friction and thermal analysis, the results are shown in Tables 1-4.

As shown from the results in Table 3, the addition of 3% by weight of co-polymer PDMS into the polyurethane synthesis, achieved the same if not lower coefficient of friction as currently lubricated polyurethane material. The current lubrication of polyurethane required an additional coating of 5% by weight addition of PDMS. This method of co-polymerizing lubrication functionality into polyurethane is more efficient at achieving lower coefficient of friction than simply coating an additional layer of PDMS.

As shown in Table 4, co-polymerization of PDMS into the resin backbone disrupted the crystallization of the hard segment but did not disturb the tensile properties.

Silicone diols, such as those disclosed in U.S. Pat. No. 4,647,643 are known products which can be prepared by synthetic methods reported in the art may be used as lubricants in the present invention. Non-silicone diols, for example fluorinated diols, such as those marketed as "Krytox" diols commercially available from Dupont may be used as lubricants in the present invention.

From consideration of the synthesis, those skilled in the art will appreciate that the silicone diol may include a mixture of functional R— groups such as a combination of ethylene and butylene groups.

A presently preferred silicone diol for use in the invention is a polydimethylsiloxane diol with molecular weight in range of 400 g/mol to 139,000 g/mol.

As a general rule, the polyurethanes of the present invention are easily prepared by forming a diol mixture containing the short chain diol, a long chain polyether or polyester diol and the silicone diol of formula and adding the diisocyanate to the diol mixture. Catalysts conventionally used in the synthesis of polyurethanes, such as dibutyltin dilaurate, tertiary amines (i.e. 1,4-diazabicyclo[2.2.2]octane), and metallic compounds (i.e. dibutyltin dilaurate or bismuth octanoate) may be used.

Polyether diols which can be used in the present invention include the polyalkylene glycols. Two polyether diols that are presently preferred for use in the present invention are poly(tetramethylene ether) glycols having molecular weights in the range of 650 to about 2000. Such polyols are commercially available as Polymeg 1000 (Quaker Oats Co., Chemical Division) and Terathane T-1000 (DuPont).

The diol included in the polyurethane resins of the invention may include ethylene glycol, 1,3-propylene glycol, 1,4-butane diol, neopentyl glycol, etc. Other diols which can be employed are alicyclic glycols having up to 10 carbon atoms, e.g., 1,4-cyclohexane diol, 1,4-dimethylol cyclohexane, etc.

Representative diisocyanates useful in the present invention include aromatic and alicyclic diisocyanates, such as 4,4-diphenyl methane diisocyanate (MDI), toluene diisocyanate (TDI), isophorone diisocyanate (IPDI), methylene bis (4-cyclohexyl isocyanate) (HMDI), etc. Of these, MDI and HMDI are presently preferred.

The diisocyanate and the diols are included in an amount of 1 to 10 weight percent of the product. In one or more embodiments, the diisocyanate range from 40% to 75% by weight. In one or more embodiments, silicone diol may be added in 1 to 10 weight %. In general, the ratio of OH to isocyanate functional group is about a 1:1 ratio.

The long chain polyether diol or the long chain polyether diol or a mixture of the two diols constitutes the balance of the polyurethane resin.

The polyurethane resins of the invention can be fabricated into film, tubing and other forms by conventional thermoplastic fabricating techniques including solution casting, extrusion molding, etc. The resin may have incorporated therein, as desired, conventional stabilizers and other additives. The amounts of these materials will vary depending upon the application of the polyurethane, but they are typically present in amounts ranging from about 0.2 to 50 weight percent of the polymer.

The polyurethane-polysiloxane resin may include polydimethylsilioxane (PDMS).

In one or more embodiments, it is envisioned that anti-microbial chemicals or anti-thrombogenic chemicals may be covalently bound to the resin.

The present invention also allows for the ability to injection mold catheters using a one shot mold without having to sacrifice optical clarity.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical article molded from a self-lubricating polyurethane-polysiloxane resin, which is a reaction product of:
   a diisocyanate comprising: 4,4-diphenyl methane diisocyanate (MDI), toluene diisocyanate (TDI), isophorone diisocyanate (IPDI), or methylene bis (4-cyclohexyl isocyanate) (HMDI); and
   a diol mixture containing:
      a short chain diol selected from the group consisting of: ethylene glycol, 1,3-propylene glycol, 1-4-butane diol, neopentyl glycol, and alicyclic glycols having up to 10 carbon atoms,
      a long chain polyether diol comprising a poly(tetramethylene ether) glycol having a molecular weight in the range of 650 to 2000, and
      a diol-containing lubricant that is polydimethylsiloxane diol according to the following structure:

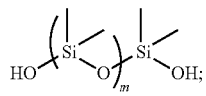

wherein m is in the range of 5 to 2000;
the diol-containing lubricant being incorporated into a backbone formed by the diisocyanate and the diol mixture;
wherein the polydimethylsiloxane diol is present in an amount ranging from about 1 to about 3 weight percent of the polyurethane-polysiloxane resin.

2. The medical article of claim 1, wherein the medical article is not implantable.

3. The medical article of claim 2, wherein the medical article is a component of a cannula, a catheter, a wedge, a tipping, a blood control actuator, a stopper, or a syringe.

4. The medical article of claim 1, wherein the polydimethylsiloxane diol has a molecular weight in the range of 400 g/mol to 77,000 g/mol.

5. The medical article of claim 1, wherein the self-lubricating polyurethane-polysiloxane resin further comprises an anti-microbial moiety, an anti-thrombogenic moiety, or both covalently attached thereto.

6. The medical article of claim 1, wherein the polyurethane-polysiloxane resin comprises a weight average molecular weight ($M_w$) in the range of from about 67,000 g/mol to 110,000 g/mol, and a number average molecular weight ($M_n$) in the range of from about 30,000 g/mol to 50,000 g/mol.

7. The medical article of claim 1, wherein the polyurethane-polysiloxane resin comprises a polydispersity in the range of from 1.8 to 2.3.

8. The medical article of claim 1, wherein the polyurethane-polysiloxane resin comprises an average tensile at break that is within one standard deviation of a comparative polyurethane resin with zero lubricant.

9. The medical article of claim 1, wherein the polyurethane-polysiloxane resin comprises a tensile at break in the range of about 3936 to about 8210 psi.

10. The medical article of claim 1 comprising a kinetic coefficient of friction of 0.215 or less in the absence of a coated lubricant.

11. A method of infusion therapy comprising:
   obtaining a medical device or a component of a medical device, the medical device or the component being molded from a self-lubricating polyurethane-polysiloxane resin that is a reaction product of:
      a diisocyanate comprising: 4,4-diphenyl methane diisocyanate (MDI), toluene diisocyanate (TDI), isophorone diisocyanate (IPDI), or methylene bis (4-cyclohexyl isocyanate) (HMDI); and
      a diol mixture containing:
         a short chain diol selected from the group consisting of: ethylene glycol, 1,3-propylene glycol, 1-4-butane diol, neopentyl glycol, and alicyclic glycols having up to 10 carbon atoms,
         a long chain polyether diol comprising a poly(tetramethylene ether) glycol having a molecular weight in the range of 650 to 2000, and
         a diol-containing lubricant that is polydimethylsiloxane diol, according to the following structure:

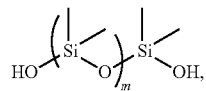

wherein m is in the range of 5 to 2000;
wherein the polydimethylsiloxane is incorporated into a backbone formed by the diisocyanate and the diol mixture and the polysiloxane is present in an amount ranging from about 1 to about 3 weight percent of the polyurethane-polysiloxane resin; and infusing a material from the medical device into a patient in the absence of a separate lubricant coated on the medical device or the component.

12. The method of claim 11, wherein the self-lubricating polyurethane-polysiloxane resin is according to Formula I:

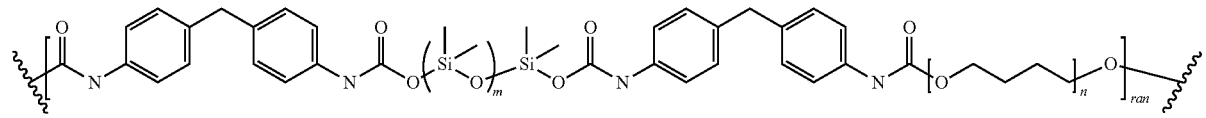

(I)

wherein the repeating unit of m is in the range from 5 to 2000; the repeating unit of n is in the range from 1 to 40, and the polyurethane resin comprises a weight average molecular weight ($M_w$) in the range of from about 67,000 g/mole to 110,000 g/mol, and a number average molecular weight ($M_n$) in the range of from about 30,000 g/mol to 50,000 g/mol; and "ran" refers to random.

* * * * *

UNITED STATES PATENT AND TRADEMARK OFFICE
CERTIFICATE OF CORRECTION

PATENT NO. : 10,995,299 B2
APPLICATION NO. : 15/959377
DATED : May 4, 2021
INVENTOR(S) : Hermel-Davidock et al.

It is certified that error appears in the above-identified patent and that said Letters Patent is hereby corrected as shown below:

In the Specification

Column 3, Line 52, replace "isocyante" with "isocyanate".

Column 3, Line 53, replace "isocyante" with "isocyanate".

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*